United States Patent
Reishus et al.

(10) Patent No.: US 8,882,720 B2
(45) Date of Patent: Nov. 11, 2014

(54) SKIN FORMULATION DISPENSER FOR USE WITH OR AS PART OF A SONIC APPLICATOR

(75) Inventors: Richard A. Reishus, Renton, WA (US); Kenneth A. Pilcher, Seattle, WA (US)

(73) Assignee: L'Oreal, Paris (FR)

( * ) Notice: Subject to any disclaimer, the term of this patent is extended or adjusted under 35 U.S.C. 154(b) by 1316 days.

(21) Appl. No.: 12/571,603

(22) Filed: Oct. 1, 2009

(65) Prior Publication Data
US 2011/0082409 A1   Apr. 7, 2011

(51) Int. Cl.
*A61M 5/00* (2006.01)
*A61M 35/00* (2006.01)

(52) U.S. Cl.
CPC .................................. *A61M 35/003* (2013.01)
USPC .......................................... 604/207; 604/246

(58) Field of Classification Search
USPC .......... 604/19–23, 207–211, 68–72, 246–256
See application file for complete search history.

(56) References Cited

U.S. PATENT DOCUMENTS 6,305,863 B1 * 10/2001 Gueret .......................... 401/126

* cited by examiner

*Primary Examiner* — Kevin C Sirmons
*Assistant Examiner* — Phillip Gray
(74) *Attorney, Agent, or Firm* — Jensen & Puntigam, PS

(57) ABSTRACT

The skin formulation dispenser includes a housing and a reservoir positioned within the housing containing a skin formulation. The dispenser includes an outlet nozzle from which the skin formulation exits and a pump assembly connecting the reservoir to the nozzle. An actuator is provided by which a user can mechanically apply pressure to the pump assembly to move the formulation from the reservoir to the nozzle. The nozzle extends from an end portion of the dispenser into a mating opening in an infuser portion of the applicator in such a manner to insure that the dispenser is authorized for use in the applicator, wherein the nozzle is configured so as to permit movement of the formulation by reasonable force from the reservoir through the nozzle while also preventing overly rapid evaporation of the formulation exiting from the nozzle.

10 Claims, 2 Drawing Sheets

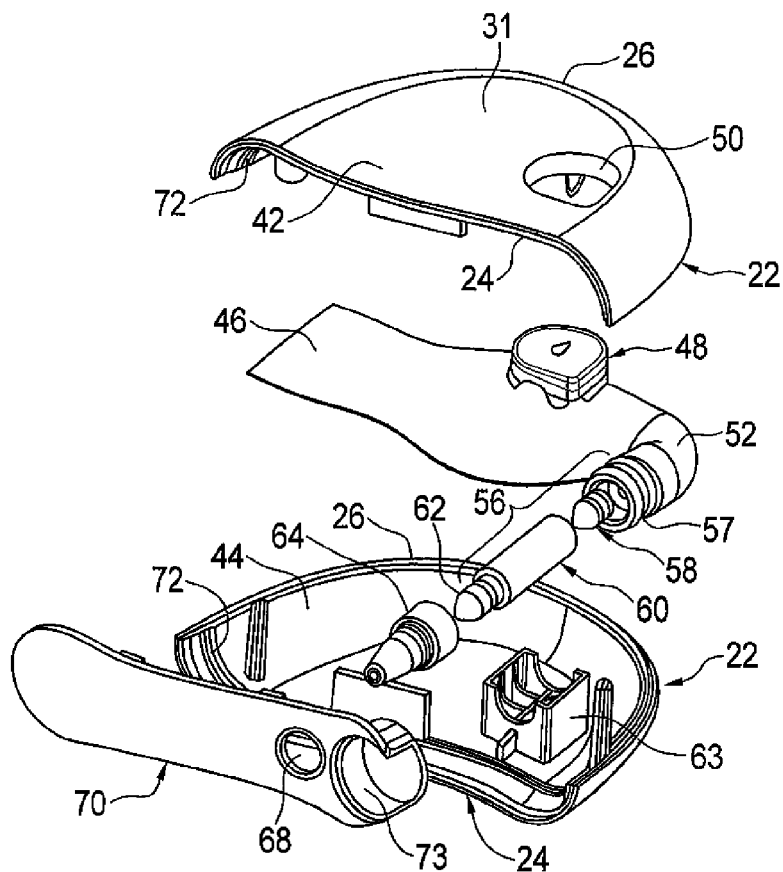
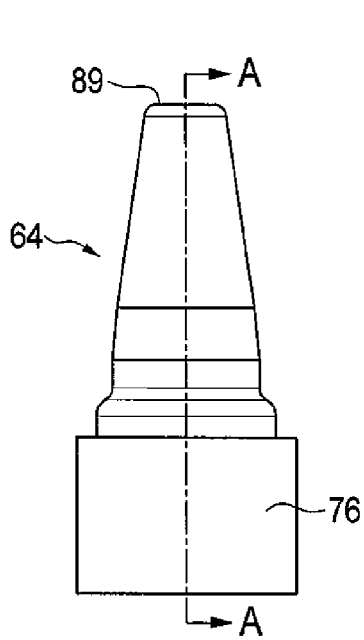
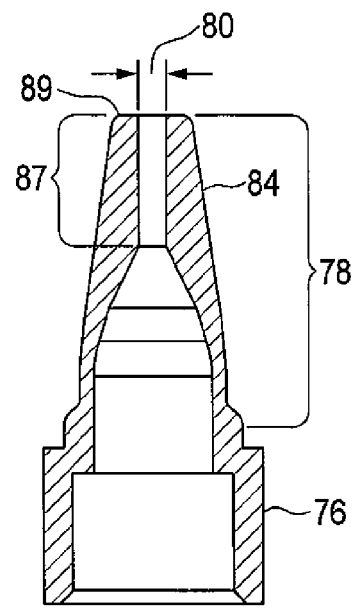
FIG. 3
FIG. 4
FIG. 5

SKIN FORMULATION DISPENSER FOR USE WITH OR AS PART OF A SONIC APPLICATOR

TECHNICAL FIELD

This invention relates generally to an applicator assembly for skin formulations, typically facial skin formulations, and more particularly concerns a skin formulation dispenser for use with or as part of the applicator assembly.

BACKGROUND OF THE INVENTION

An applicator assembly for facial skin formulations is shown in co-pending design application Ser. No. 29/337,718, and an applicator tip member portion thereof is shown in co-pending patent application Ser. No. 12/474,426. The applicator assembly and applicator tip member shown in those applications are used to apply skin formulations to the facial skin of a user. Various formulations can be used, including the application of some kinds of makeup, as well as formulations for treatment of specific skin conditions, including reduction of wrinkles, treatment of skin discoloration and other skin conditions. The formulation must be conveniently provided to the tip member portion of the applicator assembly or directly to the skin, following which the tip member is used to infuse the skin with the formulation. It is desirable that the formulation dispenser be a part of the applicator assembly so as to maintain physical integrity between the dispenser and the remainder of the applicator assembly, yet also be convenient to remove for operation of the dispenser or replacement of the dispenser when the formulation originally present in the dispenser is depleted.

SUMMARY OF THE INVENTION

Accordingly, in one aspect, the dispenser for use as a part of a skin formulation applicator assembly comprises: a dispenser housing; a reservoir positioned within the housing containing a skin formulation for treatment of a skin condition; an outlet nozzle assembly through which a skin formulation from the reservoir exits for delivery; a valve pump assembly connecting the reservoir to the nozzle; and an actuator member by which the user can move a skin formulation present in the reservoir through the nozzle, wherein the diameter of an outlet port of the nozzle has a value which permits the skin formulation to be conveniently moved, without undue effort, by user action on the actuator, while limiting evaporation of the fluid sufficiently to maintain effectiveness of the formulation, wherein the outlet port opening is within the range of 0.035 inches to 0.05 inches.

In another aspect, the dispenser for use as part of a skin formulation applicator assembly comprises: a dispenser housing which includes a lower end member which is positioned slightly inboard of a lower edge of the dispenser housing; a reservoir positioned within the housing containing a skin formulation; and a delivery assembly, including a nozzle, for delivering the skin formulation from the reservoir to the nozzle portion by a user operating an actuating mechanism, wherein the nozzle includes a portion which extends beyond the end member, the extending portion configured to just fit into a mating opening in an infuser portion of the applicator assembly, providing an assurance that the dispenser is authorized for use in the applicator assembly.

BRIEF DESCRIPTION OF THE DRAWINGS

FIG. 3 is an exploded view of the dispenser portion of the applicator assembly.
FIG. 4 is an elevational view of a nozzle portion of the dispenser of FIG. 3.
FIG. 5 is a cross-sectional view of the nozzle of FIG. 4 taken along lines 5-5 thereof.

BEST MODE FOR CARRYING OUT THE INVENTION

Figure 1:
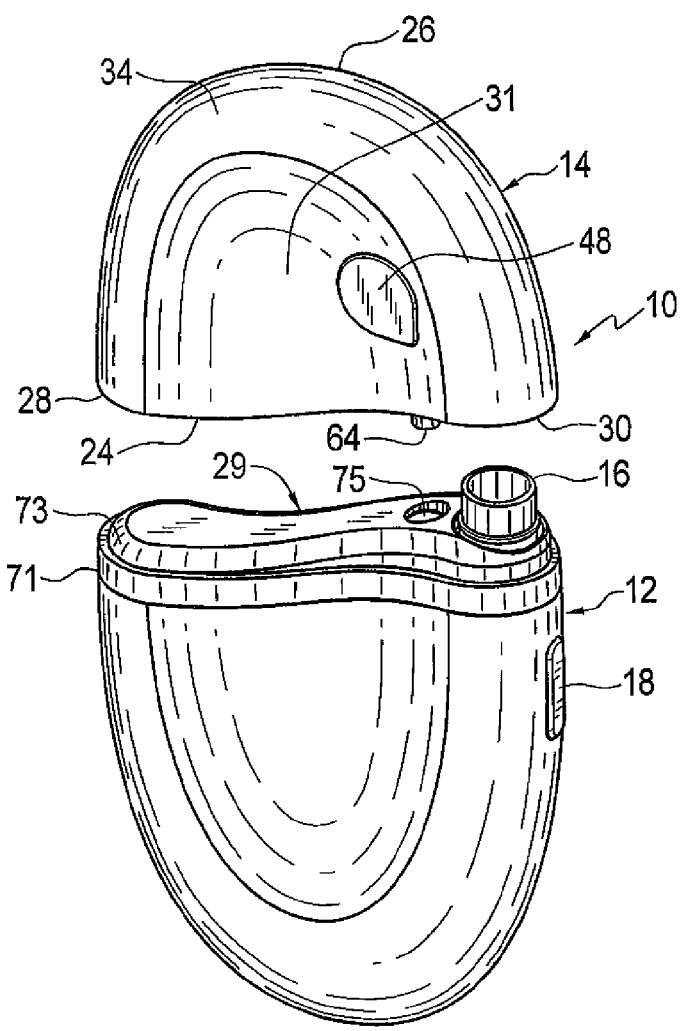
FIG. 1 is a perspective view of the complete applicator assembly for skin formulations, including an infuser portion and a dispenser portion.
Figure 2:
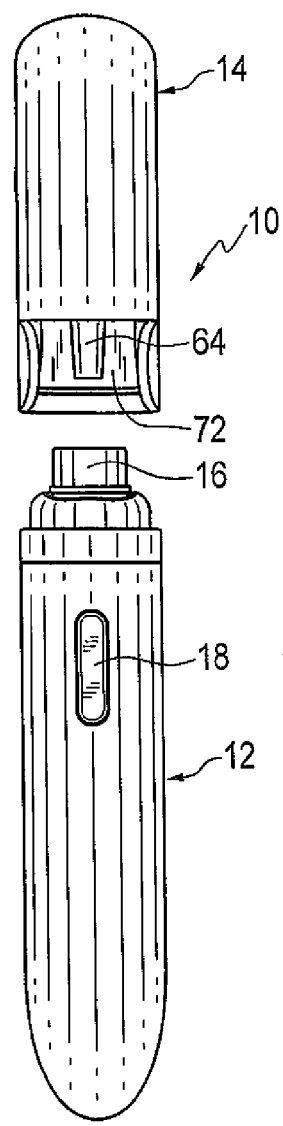
FIG. 2 is a side view of the applicator assembly of FIG. 1.

FIGS. 1 and 2 show an applicator assembly, generally at 10, for applying skin formulations, primarily facial skin formulations, to the skin, primarily facial skin, of a user. It is possible, however, to use the applicator assembly with other skin areas. In FIGS. 1 and 2, the applicator assembly comprises two portions; an infuser portion 12 and a dispenser portion 14. Such an applicator assembly is shown in detail in the '718 design application, the contents of which are incorporated herein by reference. The infuser portion includes an applicator tip member 16 which comprises a relatively soft material for contact with the skin. The tip member is described in the '426 application, the contents of which are also incorporated herein by reference. The infuser 12 operates typically in a sonic frequency range of 50-200 Hz, with a preferred range of 100-140 Hz. The infuser 12 includes a motor, a battery and a microprocessor controller which are not shown specifically in FIG. 1, but are shown and described in an applicator assembly, in co-pending patent application Ser. No. 12/135,887, the contents of which are also incorporated herein by reference. Infuser 12 is controlled by an on/off switch 18.

In operation of the applicator assembly, dispenser 14 is removed by the user from infuser 12 and a small amount of skin formulation in a reservoir in the dispenser is dispensed either directly onto the facial skin of the user at the desired treatment location, or into tip member 16. The user then operates the on/off switch 18 on the infuser while positioning the tip member against the desired skin location. In operation, the motor in the infuser drives the tip member back and forth through a selected distance, typically in the range of 0.01-0.075 inches. The moving tip member infuses the skin formulation into the facial skin of the user at the desired location.

Dispenser 14 is shown in more detail in FIG. 3. The dispenser includes a housing 22 which in the embodiment shown is made from a plastic material. It includes a front section 42, a back section 44 and an end or web member 70. Housing 22 includes a wavy bottom edge 24 and a curved upper edge 26 which extends from one end 28 of the bottom edge 24 to the other end 30 thereof. Wavy edge 24 is generally configured to mate tightly with a corresponding wavy upper edge 29 of infuser 12. Dispenser 14 includes a central area 31 which is slightly depressed or concave relative to edge portion 34. The overall exterior configuration of dispenser 14, as shown, matches the configuration of the infuser portion, as shown most clearly in FIG. 1 herein and the '718 design application.

Referring to FIG. 3, mounted within dispenser 14 is a pouch reservoir 46 which contains a quantity of skin formulation, in the embodiment shown approximately 10-12 mL. Again, the skin formulation can vary; in one particular embodiment it can be a liquid formulation to reduce fine lines or wrinkles. Other skin formulations can be used to treat other skin conditions. Pouch 46 can have a variety of configurations to fit conveniently within the interior of the dispenser 14. An actuator button 48 extends through an opening 50 in front section 42 of the dispenser. The actuator button, when pressed by a user, exerts a pressure on a pump tube 60, which is part of a pump assembly 56, forcing a quantity of skin formulation therein out through an exit valve 62, which is also part of the pump assembly 56. Portions of the pump assembly 56, including pump tube 60, are supported by support member 63. Pouch 46 in the embodiment shown is made from a flexible material, such as PVC, PE or PET or a combination thereof.

Pouch 46 includes an exit portion 52; extending away therefrom is a proximal valve body 57. In the embodiment shown, proximal valve body 57 includes a proximal or inflow one-way check valve 58 which is connected to one end of pump tube 60, which in turn is connected to a distal or outflow one-way check valve 62. The output of check valve 62 is applied to the input of a nozzle 64. Nozzle 64 extends through an opening 68 in web member 70 which closes the end of housing 22 between front and rear sections 42 and 44 thereof. Web 70 fits into a groove 72 in the internal surfaces of sections 42 and 44 a short distance inboard from wavy edge 24. The interior surfaces of sections 42 and 44 forwardly of web 70 are configured to mate with the exterior edge surface of infuser 12, providing a tight frictional fit, aligning the dispenser with the infuser. Dispenser 14 will then tend to stay connected to the infuser 12 by the fit and/or by means of attracting magnets on the infuser and either magnets or ferromagnetic members of steel or the like on the dispenser, or vice versa, until positively removed by the user. The surface configuration includes two peripheral sections 71 and 73 on the infuser and mating sections on the dispenser. This helps in ensuring that only authentic/authorized dispensers are used in the applicator assembly.

Web 70 includes a cavity 73 into which the tip member of the infuser fits when the dispenser 14 is fitted onto the infuser 12. While FIGS. 1, 2 and 3 in particular show nozzle 64 being spaced apart from cavity 73, it should be understood that the nozzle could be positioned so that the fluid formulation from the pouch 46 can be directed through the nozzle to the tip member 16, in particular the dish-shaped upper portion of the tip member. This can be accomplished either when the dispenser and the infuser are mated together or when the user separates the two and positions the dispenser so that fluid from the nozzle is directed into the tip member.

The upper surface of the infuser includes an opening 75 (FIG. 1) into which the nozzle 64 fits when the dispenser is properly mated to the infuser. Opening 75 is configured relative to the shape of nozzle 64 to permit entry of the nozzle, preferably a tight fit. The size of the opening and the configuration of the nozzle also help insure that replacement dispensers are authentic/authorized for the applicator assembly.

FIGS. 4 and 5 show the details of nozzle 64. Nozzle 64 generally includes a base portion 76 and an extending portion 78. Extending portion 78 is that part of nozzle 64 which protrudes from housing 22, i.e. through opening 68 in web 70. Generally, nozzle 64 comprises a hard ABS plastic material, and while the shape of the nozzle varies along the length thereof, it is generally always circular in cross-section. The particular configuration of the nozzle, which is explained in more detail below, makes it well suited for the reliable and convenient transport and delivery of a viscous fluid provided to it from reservoir pouch 46.

The configuration of the nozzle is such as to permit convenient dispensing of fluid from the pouch by the user's action, without excessive force, on the actuator button 48 and is also arranged to be inexpensive to manufacture. As indicated above, nozzle 64 extends from and encloses the distal/outflow check valve 62 and the outflow end of pump tube 60. Fluid exits from an outlet port 80 of the nozzle. The various nozzle configuration parameters described below are important for the overall operation of the nozzle, the dispensing portion and hence the applicator assembly as a whole. The nozzle is designed to give optimal performance. Nozzle dimensions which fall outside of the ranges specified below will result in either poor performance, unacceptable difficulty to use, and/or higher costs in manufacture.

The diameter of output port 80, i.e. the nozzle opening, has a preferred value of 0.04 inches. An acceptable range of the opening is from 0.025 inches to 0.05 inches. The minimum diameter (lower end of range) is determined by the viscosity of the dispensed fluid as well as the consideration of low cost injection molding, while the maximum diameter (upper end of the range) is determined by the maximum permissible evaporation of the dispensed fluid, which increases as the opening gets larger. A value lower than the minimum range limit makes it too difficult for the liquid to flow with reasonable ease with the pumping force generated by the human user. A reasonable maximum pumping force for the average user is approximately 5 lbs. An output port opening larger than the maximum range limit results in too rapid evaporation of the dispensed fluid. An optimum value of 0.04 inches provides the best balance of low cost, reasonable necessary pumping force and an acceptable amount of fluid evaporation.

A second significant aspect of the geometry of the nozzle is the ratio of the diameter of outlet port 80 to the length of the outlet port, referred to at 87. The optimum ratio value has been determined to be 1:4.8, while ratios between 1:3 and 1:6 provide acceptable results relative to pumping force limit and an acceptable evaporation value. The optimal ratio provides the best balance between a reasonable value of pumping force for formulation discharge and an acceptable rate of fluid evaporation. Ratios below 1:4.8 produced unacceptable rates of fluid evaporation, while ratios above 1:6 resulted in unacceptable high pumping force requirements.

The outside diameter of the nozzle end surface, referred to at 89, is also considered to be important. An optimal value of end surface diameter has been determined to be 0.125 inches, with values between 0.05 to 0.20 inches being acceptable. Diameters larger than 0.20 are unacceptable due to the tendency for the dispensed fluid to accumulate at the end of the nozzle, causing difficulties in transfer of the formulation to the tip member 16 and a waste of fluid. Diameters below 0.05 resulted in difficulties in low-cost injection molding manufacture, an important consideration for the nozzle.

The optimum value of the overall length of the protruding portion 78 of the nozzle is 0.435 inches, with an acceptable range between 0.30 inches and 0.475 inches. Length is important to permit the user to have full visual access of the end of the nozzle during dispensing so that the user can correctly position the nozzle on the face or to the tip member, while the length is limited to prevent interference with the infusing portion of the applicator assembly.

As discussed above, nozzle 64 has a varying cross-sectional configuration along its length. However, the portion of the length of the nozzle shown in FIG. 5 referenced by numeral 84 is preferably a truncated cone, with a taper angle of approximately 7.1°, although this can be varied.

Hence, a dispensing portion of a skin formulation applicator has been disclosed. It includes a particular configuration and arrangement of the nozzle portion thereof which allows formulation fluid to be dispensed with a reasonable user force and without undue evaporation. Further, aspects of the physical interface/connection between the dispenser and the infuser portions of the applicator assembly assist in insuring that only authentic dispensers, including replacement dispensers, are used in the applicator assembly.

Although a preferred embodiment has been disclosed for purposes of illustration, it should be understood that various changes and modifications and substitutions could be made in the preferred embodiment without departing from the spirit of the invention as defined by the claims which follow:

What is claimed is:

1. A dispenser for use as part of a skin formulation applicator assembly, comprising:
   a dispenser housing which includes a lower end member which is positioned slightly inboard of a lower edge of the dispenser housing;
   a reservoir positioned within the housing containing a skin formulation; and
   a delivery assembly, including a nozzle, for delivering the skin formulation from the reservoir to the nozzle portion by a user operating an actuating mechanism, wherein the nozzle includes a portion which extends beyond the end member, the extending portion configured to just fit into a mating opening in an infuser portion of the applicator assembly, providing an assurance that the dispenser is authorized for use in the applicator assembly.

2. The dispenser of claim 1, wherein the lower end member further includes a cavity to receive a tip member part of the infuser portion when the dispenser is mated with the infuser.

3. The dispenser of claim 1, wherein an interior surface of the dispenser inboard of the lower edge thereof is configured to mate tightly with an upper edge portion of the infuser, aligning the dispenser with the infuser portion, so that magnetic attraction members on the dispenser and the infuser portion can tend to prevent the dispenser and the infuser portion from separating.

4. The dispenser of claim 3, wherein the lower edge of the dispenser has a wavy configuration which mates with a corresponding wavy configuration of the upper edge of the infuser.

5. The dispenser of claim 1, wherein the nozzle includes an outlet port with an outlet port opening having a diameter which permits the skin formulation to be conveniently moved, without undue effort, by user action on the actuating mechanism, while limiting evaporation of the formulation sufficiently to maintain effectiveness of the formulation, wherein the diameter of the outlet port opening is within the range of 0.025 inches to 0.05 inches.

6. The dispenser of claim 5, wherein the diameter of the outlet port opening is approximately 0.04 inches.

7. The dispenser of claim 1, wherein the ratio of the diameter of the outlet port opening to the length of the outlet port is within the range of 1:3 to 1:6.

8. The dispenser of claim 1, wherein the nozzle has an outlet end with an outside diameter within the range of 0.05 to 0.20 inches.

9. The dispenser of claim 1, wherein the length of the extending portion is within the range of 0.30 inches to 0.475 inches.

10. The dispenser of claim 1, wherein the exterior surface of the nozzle is configured to just fit within an opening in the upper surface of an infuser portion of the applicator assembly, providing a reliable mating between the dispenser portion and the infuser portion and an indication that the dispensing portion is an authorized part of the applicator assembly.

* * * * *